United States Patent [19]

Rivier et al.

[11] Patent Number: 4,569,927
[45] Date of Patent: Feb. 11, 1986

[54] GNRH ANTAGONISTS IV

[75] Inventors: Jean E. F. Rivier; Wylie W. Vale, Jr., both of La Jolla, Calif.

[73] Assignee: The Salk Institute For Biological Studies, San Diego, Calif.

[21] Appl. No.: 612,072

[22] Filed: May 21, 1984

Related U.S. Application Data

[63] Continuation-in-part of Ser. No. 583,093, Feb. 23, 1984, which is a continuation-in-part of Ser. No. 512,920, Jul. 12, 1983, abandoned, which is a continuation-in-part of Ser. No. 473,876, Mar. 10, 1983, abandoned.

[51] Int. Cl.$^4$ .................... C07C 103/52; A61K 37/02
[52] U.S. Cl. ............................ 514/15; 260/112.5 LH; 260/112.5 R
[58] Field of Search ............... 260/112.5 LH; 424/177

[56] References Cited

U.S. PATENT DOCUMENTS

| 4,317,815 | 3/1982 | Coy et al. | 260/112.5 LH |
| 4,341,767 | 7/1982 | Nestor et al. | 260/112.5 LH |
| 4,444,759 | 4/1984 | Rivier et al. | 260/112.5 LH |

OTHER PUBLICATIONS

Coy et al., *Endocrinology*, vol. 110, No. 4, 1982, pp. 1445–1447.
Yabe et al., "Synthesis and Biological Activity of LH-RH Analogs Substituted by Alkyltryptophans at Position 3$^1$)", *Chem. Pharm. Bull.*, 27(8) 1907–1911, (1979).

*Primary Examiner*—Delbert R. Phillips
*Assistant Examiner*—F. T. Moezie
*Attorney, Agent, or Firm*—Fitch, Even, Tabin & Flannery

[57] ABSTRACT

Peptides which inhibit the secretion of gonadotropins by the pituitary gland and inhibit the release of steroids by the gonads. Administration of an effective amount prevents ovulation of female mammalian eggs and/or the release of steroids by the gonads. The peptides have the structure:

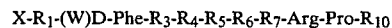

$X-R_1-(W)D-Phe-R_3-R_4-R_5-R_6-R_7-Arg-Pro-R_{10}$ wherein X is hydrogen or an acyl group having 7 or less carbon atoms; $R_1$ is dehydro-Pro, D-pGlu, D-Phe, D-Trp of β-D-NAL; W is F, Cl, Cl$_2$ Br, NO$_2$ or C$^\alpha$Me-Cl; $R_3$ is (N$^{in}$For)D-Trp or D-Trp which is substituted in the 5- or 6-position with NO$_2$, NH$_2$, OCH$_3$, F, Cl, Br or CH$_3$; $R_4$ is Ser, Orn, AAL or aBu; $R_5$ is Tyr, Arg, (3F)Phe, (2F)Phe, (3I)Tyr, (3CH$_3$)Phe, (2CH$_3$)Phe, (3Cl)Phe or (2Cl)Phe; $R_6$ is (4NH$_2$)D-Phe, D-Lys, D-Orn, D-Har, D-His, (4gua)D-Phe, D-Tyr, a D-isomer of a lipophilic amino or D-Arg; $R_7$ is Leu, NML, Nle or Nva; and $R_{10}$ is Gly-NH$_2$, D-Ala-NH$_2$ or NH-Y, with Y being lower alkyl, cycloalkyl, fluoro lower alkyl or

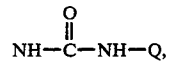

$$NH-\overset{\overset{\displaystyle O}{\|}}{C}-NH-Q,$$

where Q is H or lower alkyl, provided however that when $R_5$ is Arg, $R_6$ is D-Tyr.

21 Claims, No Drawings

GNRH ANTAGONISTS IV

This invention was made with Government support under Grant No. HD-13527 awarded by the National Institutes of Health. The Government has certain rights in this invention.

This application is a continuation-in-part of our application Ser. No. 583,093, filed Feb. 23, 1984, which is a continuation-in-part of our application Ser. No. 512,920, filed July 12, 1983, abandoned, which is a continuation-in-part of our application Ser. No. 473,876, filed Mar. 10, 1983, abandoned.

The present invention relates to peptides which inhibit the release of gonadotropins by the pituitary gland in mammalians, including humans, and to methods of preventing ovulation and/or inhibiting the release of steroids. More particularly, the present invention is directed to peptides which inhibit gonadal function and the release of the steroidal hormones, progesterone and testosterone.

BACKGROUND OF THE INVENTION

The pituitary gland is attached by a stalk to the region in the base of the brain known as the hypothalamus. In particular, follicle stimulating hormone (FSH) and luteinizing hormone (LH), sometimes referred to as gonadotropins or gonadotropic hormones, are released by the pituitary gland. These hormones, in combination, regulate the functioning of the gonads to produce testosterone in the testes and progesterone and estrogen in the ovaries, and they also regulate the production and maturation of gametes.

The release of a hormone by the anterior lobe of the pituitary gland usually requires a prior release of another class of hormones produced by the hypothalamus. One of the hypothalamic hormones acts as a factor that triggers the release of the gonadotropic hormones, particularly LH, and this hormone is referred to herein as GnRH although it has also been referred to as LH-RH and as LRF. GnRH has been isolated and characterized as a decapeptide having the following structure:

p-Glu-His-Trp-Ser-Tyr-Gly-Leu-Arg-Pro-Gly-NH$_2$

Peptides are compounds which contain two or more amino acids in which the carboxyl group of one acid is linked to the amino group of the other acid. The formula for GnRH, as represented above, is in accordance with conventional representation of peptides where the amino terminus appears to the left and the carboxyl terminus to the right. The position of the amino acid residue is identified by numbering the amino acid residues from left to right. In the case of GnRH, the hydroxyl portion of the carboxyl group of glycine has been replaced with an amino group (NH$_2$). The abbreviations for the individual amino acid residues above are conventional and are based on the trivial name of the amino acid, e.g. p-Glu is pyroglutamic acid, His is histidine, Trp is tryptophan, Ser is serine, Tyr is tyrosine, Gly is glycine, Leu is leucine, Orn is ornithine, Arg is arginine, Pro is proline, Phe is phenylalanine and Ala is alanine. These amino acids together with valine, isoleucine, threonine, lysine, aspartic acid, asparagine, glutamine, cysteine, methionine, phenylalanine, and proline are generally considered to be the common, naturally occurring or protein-derived amino acids. Except for glycine, amino acids of the peptides of the invention are of the L-configuration unless noted otherwise.

It is well known that the substitution of D-amino acids for Gly in the 6-position of the GnRH decapeptide or nonapeptide provides GnRH analogs having substantially greater binding affinity and thus can be used to produce both agonists and antagonists of higher potency. It is also known that substitution of various amino acids for His (or the deletion of His) at the 2-position of the GnRH decapeptide produces anatagonists having an inhibitory effect on the release of LH and other gonadotropins by the pituitary gland of mammalians. The releasing or inhibitory effect is obtained when the GnRH analog is administered to a mammalian intravenously, subcutaneously, intramuscularly, orally, percutaneously, e.g. intranasally, or intravaginally.

There are reasons for desiring to prevent ovulation in female mammalians, and the administration of GnRH analogs that are antagonistic to the normal function of GnRH have been used to suppress or delay ovulation. For this reason, analogs of GnRH which are antagonistic to GnRH are being investigated for their potential use as a contraceptive or for regulating conception periods. GnRH antagonists may also be used for the treatment of precocious puberty and endometriosis to promote growth in female animals. Such antagonists have also been found useful to regulate the secretion of gonadotropins in male mammals and can be employed to arrest spermatogenesis, e.g. as male contraceptives, and for treatment of prostatic hypertrophy. It is desired to provide improved peptides which are strongly antagonistic to endogenous GnRH and which prevent secretion of LH and the release of steroids by the gonads of mammals.

SUMMARY OF THE INVENTION

The present invention provides peptides which inhibit the release of gonadotropins in mammalians, including humans, and it also provides methods for inhibiting the release of steroids by the gonads of male and female mammalians. The improved GnRH analogs are strongly antagonistic to GnRH and have an inhibitory effect on the reproduction processes of mammalians. These analogs may be used to inhibit the production of gonadotropins and sex hormones under various circumstances including precocious puberty, hormone dependent neoplasia, dysmenorrhea and endometriosis.

Generally, in accordance with the present invention, peptides have been synthesized which strongly inhibit the secretion of gonadotropins by the pituitary gland of mammalians, including humans, and/or inhibit the release of steroids by the gonads. These peptides are analogs of GnRH wherein there is a 1-position substitution, such as dehydro-Pro, D-pGlu, D-Phe, D-Trp or β-(2-naphthyl)-D-alanine (hereinafter β-D-2NAL), a 2-position substitution in the form of a substituted, e.g., halogenated, D-Phe, a 3-position substitution, an optional substitution of a diamino acid having not more than 5 carbon atoms in the 4-position, an optional substitution in the 5-position in the form of a halogenated L-Phe or L-Tyr, or the combined substitution of Arg in the 5-position and D-Tyr in the 6-position, a 6-position substitution and optional substitutions in the 7- and 10-positions. The 1-position substituent may be modified so that its alpha amino group contains an acyl group, such as formyl, acetyl, acrylyl, vinylacetyl(Vac) or benzoyl(Bz), with acetyl(Ac) and acrylyl(Acr) being preferred. Modified D-Trp in the 3-position provides increased antagonistic activity as a result of the specific modifications present in the indole ring. Single substitutions for hydrogen are made in either the 5- or 6-position, and the substitutions are selected from chloro, fluoro, bromo, methyl, amino, methoxy and nitro, with chloro, fluoro and nitro being preferred. The indole nitrogen may also be acylated, e.g. with formyl ($N^{in}$-For- or 1For-) or with acetyl. When β-D-NAL is present in the 1-position, a hydrophillic D-amino acid residue, such as (4NH$_2$)D-Phe, 4guanidino-D-Phe, D-His, D-Lys, D-Orn, D-Arg or D-Har(Homoarginine) is preferably present in the 6-position. When dehydro-Pro is present in the 1-position, a D-isomer of a lipophilic amino acid, such as D-Trp, D-Phe, D-Leu, D-Ile, D-Nle, D-Try, D-Val, D-Ala, D-Ser(OtBu), β-D-2NAL or (imBzl)D-His is preferably present in the 6-position. As mentioned above, the substitutions in the 4-,7- and 10-positions are generally considered to be optional.

Because these peptides are highly potent to inhibit release of LH, they are often referred to as GnRH antagonists. The peptides inhibit ovulation of female mammals when administered at very low levels at proestrus and are also effective to cause resorption of fertilized eggs if administered shortly after conception. These peptides are also effective for the contraceptive treatment of male mammals.

DETAILED DESCRIPTION OF THE PREFERRED EMBODIMENTS

More specifically, the peptides of the present invention are represented by the following Formula I:

wherein X is hydrogen or an acyl group having 7 or less carbon atoms; R$_1$ is dehydro-Pro, D-pGlu, D-Phe, D-Trp or β-D-NAL; W is F, Cl, Cl$_2$ Br, NO$_2$ or C$^α$Me-Cl; R$_3$ is ($N^{in}$For)D-Trp or D-Trp which is substituted in the 5- or 6-position with NO$_2$, NH$_2$, OCH$_3$, F, Cl, Br or CH$_3$; R$_4$ is Ser, Orn, AAL or aBu; R$_5$ is Tyr, Arg, (3F)Phe, (2F)Phe, (3I)Tyr, (3CH$_3$)Phe, (2CH$_3$)Phe, (3Cl)Phe or (2Cl)Phe; R$_6$ is A(4NH$_2$)D-Phe, D-Lys, D-Orn, D-Har, D-His, (4gua)D-Phe, D-Tyr, a D-isomer of a lipophilic amino or D-Arg; R$_7$ is Leu, NML, Nle or Nva; and R$_{10}$ is Gly-NH$_2$, D-Ala-NH$_2$ or NH-Y, with Y being lower alkyl, cycloalkyl, fluoro lower alkyl or

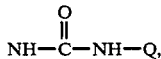

where Q is H or lower alkyl, provided however that when R$_5$ is Arg, R$_6$ is D-Tyr.

By β-D-NAL is meant the D-isomer of alanine which is substituted by naphthyl on the β-carbon atom, which may also be designated 3-D-NAL. Preferably β-D-2NAL is employed which means that the β-carbon atom is attached to naphthalene at the 2-position on the ring structure; however, β-D-1NAL may also be used. By NML is meant N$^α$CH$_3$-L-Leu. By (C$^α$Me-4Cl)Phe is meant a phenylalanine residue that is substituted with chlorine in the para-position and the alpha-carbon atom of which is methylated. By AAL is meant β-amino-Ala and by a Bu is meant α,γ diamino butyric acid, either of which or Orn can be present in the 4-position. When Ser is not present in the 4-position, dehydro Pro is preferably present in the 1-position.

The peptides of the present invention can be synthesized by classical solution synthesis or by a solid phase technique using a chloromethylated resin, a methylbenzhydrylamine resin (MBHA), a benzhydrylamine (BHA) resin or any other suitable resin known in the art. The solid synthesis is conducted in a manner to stepwise add the amino acids in the chain in the manner set forth in detail in the U.S. Pat. No. 4,211,693. Side-chain protecting groups, as are well known in the art, are preferably added to Ser, Tyr and Arg when present, as well as to certain of the substituents, and may optionally be added to Trp (unless acylated), before these amino acids are coupled to the chain being built upon the resin. Such a method provides the fully protected intermediate peptidoresin.

The intermediates of the invention may be represented by Formula II:

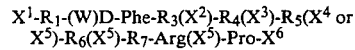

wherein: $X^1$ is an α-amino protecting group of the type known to be useful in the art in the stepwise synthesis of polypeptides and when X in the desired peptide composition is a particular acyl group, that group may be used as the protecting group. Among the classes of α-amino protecting groups covered by $X^1$ are (1) acyl-type protecting groups, such as formyl(For), fluoroacetyl, phthalyl, p-toluenesulfonyl(Tos), benzoyl(Bz), benzenesulfonyl, o-nitrophenylsulfenyl(Nps), tritylsulfenyl, o-nitrophenoxyacetyl, acrylyl(Acr), chloroacetyl, acetyl-(Ac) and γ-chlorobutyryl; (2) aromatic urethan-type protecting groups, e.g., benzyloxycarbonyl (Z) and substituted benzoyloxycarbonyl, such as p-chloro-benzyloxycarbonyl (ClZ), p-nitrobenzyloxycarbonyl, p-bromobenzyloxycarbonyl and p-methoxybenzyloxycarbonyl, (3) aliphatic urethan protecting groups, such as tertbutyloxycarbonyl(Boc), diisopropylmethoxycarbonyl, isopropyloxycarbonyl, ethoxycarbonyl and allyloxycarbonyl; (4) cycloalkyl urethan-type protecting groups, such as cyclopentyloxycarbonyl, adamantyloxycarbonyl and cyclohexyloxycarbonyl; (5) thiourethan-type protecting groups, such as phenylthiocarbonyl; (6) alkyl-type protecting groups, such as allyl(Aly), triphenylmethyl(trityl) and benzyl(Bzl); (7) trialkylsilane groups, such as trimethylsilane. The preferred α-amino protecting group is Boc when X is hydrogen.

$X^2$ is hydrogen or a protecting group for the indole nitrogen, such as formyl or benzyl. In many syntheses there is no need to protect the indole NH of Trp; however $X^2$ is formyl when R$_3$ is ($N^{in}$For)D-Trp.

$X^3$ is hydrogen or a protecting group for the alcoholic hydroxyl group of Ser, such as one selected from the group consisting of acetyl, benzoyl, tetrahydropyranyl, tert-butyl, trityl, benzyl and 2,6-dichlorobenzyl, with benzyl being preferred. Alternatively, when a substitution is made for Ser, $X^3$ may be a protecting group for a side chain amino group, such as Tos, Z or ClZ.

$X^4$ is hydrogen or a protecting group for the phenolic hydroxyl group of Try, if Tyr is present, selected from the group consisting of tetrahydropyranyl, tert-butyl, trityl, benzyl, Z, 4-bromobenzyloxycarbonyl and 2,6-dichlorobenzyl. 2,6-dichlorobenzyl is preferred.

$X^5$ is a protecting group for the side chain guanidino group of Arg; for the Lys side chain amino group or the His imidazole group, such as nitro, Tos, trityl, benzyloxycarbonyl, adamantyloxycarbonyl, Z and Boc; for Tyr such as X4; for Trp such as X2; or X5 may be hydrogen, which means there is no protection on the side chain group atoms. Tos is generally preferred for Arg.

$X^6$ may be Gly-O-CH$_2$-[resin support]; O-CH$_2$-[resin support]; D-Ala-O-CH$_2$-[resin support]; Gly-NH-[resin support] or D-Ala-NH-[resin support]; and it may be OH, ester, amide or hydrazide either of Gly or of D-Ala or attached directly to Pro.

The criterion for selecting side chain protecting groups for $X^2$–$X^5$ is that the protecting group should be stable to the reagent under the reaction conditions selected for removing the α-amino protecting group at each step of the synthesis. The protecting group should not be split off under coupling conditions, and the protecting group should be removable upon completion of the synthesis of the desired amino acid sequence under reaction conditions that will not alter the peptide chain.

When the $X^6$ group is Gly-O-CH$_2$-[resin support], D-Ala-O-CH$_2$-[resin support] or O-CH$_2$-[resin support], the ester moiety of one of the many functional groups of the polystyrene resin support is being represented. When the $X^6$ group is Gly-NH-[resin support] or D-Ala-NH-[resin support], an amide bond connects Gly or D-Ala to BHA resin or to a MBHA resin.

When X is acetyl, for example, in the final formula, it may be possible to employ it as the $X^1$ protecting group for the α-amino group of D-NAL or whatever amino acid is used in the 1-position by adding it before the coupling of this last amino acid to the peptide chain. However, a reaction is preferably carried out with the peptide on the resin (after deblocking the α-amino group while the side-chain groups remain protected), e.g. by reacting with acetic acid in the presence of dicyclohexyl carbodiimide(DCC) or preferably with acetic anhydride or by another suitable reaction as known in the art.

The fully protected peptide can be cleaved from a chloromethylated resin support by ammonolysis, as is well known in the art, to yield the fully protected amide intermediate. Deprotection of the peptide, as well as cleavage of the peptide from a benzhydrylamine resin, can take place at 0° C. with hydrofluoric acid (HF). Anisole is preferably added to the peptide prior to treatment with HF. After the removal of HF under vacuum, the cleaved, deprotected peptide is conveniently treated with ether, decanted, taken-up in dilute acetic acid and lyophilized.

Thus, the invention also provides a method for making a peptide having Formula I or a nontoxic salt thereof, which method comprises (a) forming an intermediate compound having the Formula II:

$$X^1\text{-}R_1\text{-(W)D-Phe-}R_3(X^2)\text{-}R_4(X^3)\text{-}R_5(X^4)\text{-}R_6(X^5)\text{-}R_7\text{-Arg}(X^5)\text{-Pro-}X^6$$

wherein $X^1$ is hydrogen or an α-amino protecting group; $X^2$ is hydrogen or a protecting group for the indole nitrogen; $X^3$ is hydrogen or a protecting group for the alcoholic hydroxyl group of Ser or for a side-chain amino group; $X^4$ is hydrogen or a protecting group for the phenolic hydroxyl group of Tyr; $X^5$ is hydrogen or a suitable side-chain protecting group; and $X^6$ is selected from the group consisting of Gly-O-CH$_2$-(resin support), O-CH$_2$-(resin support), D-Ala-O-CH$_2$-(resin support), Gly-NH-(resin support), D-Ala-NH-(resin support), Gly-NH$_2$, and esters, amides and hydrazides; (b) splitting off one or more of the groups $X^1$ to $X^5$ and/or cleaving from any resin support included in $X^6$ and, if desired, (c) converting a resulting peptide into a nontoxic salt thereof.

Purification of the peptide is effected by ion exchange chromotography on a CMC column, followed by partition chromotography using the elution system: n-butanol; 0.1N acetic acid (1:1 volume ratio) on a column packed with Sephadex G-25, or by using HPLC, as known in the art.

The peptides of the invention are effective at levels of less than 100 micrograms per kilogram of body weight, when administered at about noon on the day of proestrus, to prevent ovulation in female rats. For prolonged suppression of ovulation, it may be necessary to use dosage levels in the range of from about 0.1 to about 2.5 milligrams per kilogram of body weight. These antagonists are also effective to arrest spermatogenesis when administered to male mammals on a regular basis and can thus be used as contraceptives. Since these compounds will reduce testosterone levels (an undesired consequence in the normal, sexually active male), it may be reasonable to administer replacement dosages of testosterone along with the GnRH antagonist. These antagonists can also be used to regulate the production of gonadotropins and sex steroids for other purposes as indicated hereinbefore.

EXAMPLE I

Peptides as indicated in TABLE I having the formula:

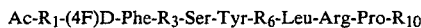

Ac-R$_1$-(4F)D-Phe-R$_3$-Ser-Tyr-R$_6$-Leu-Arg-Pro-R$_{10}$ are prepared by the solid-phase procedure referred to above.

TABLE I

| | R$_1$ | R$_3$ | R$_6$ | R$_{10}$ |
|---|---|---|---|---|
| 1 | β-D-2NAL | (6NO$_2$)D-Trp | D-Arg | Gly-NH$_2$ |
| 2 | " | " | " | D-Ala-NH$_2$ |
| 3 | dehydro Pro | " | β-D-2NAL | Gly-NH$_2$ |
| 4 | β-D-2NAL | (6NH$_2$)D-Trp | D-Arg | " |
| 5 | " | (5OCH$_3$)D-Trp | " | " |
| 6 | " | (5Br)D-Trp | " | " |
| 7 | " | (5F)D-Trp | " | " |
| 8 | " | (5Cl)D-Trp | " | " |
| 9 | " | (5CH$_3$)D-Trp | " | Gly-NH$_2$ |
| 10 | β-D-2NAL | (N$^{in}$For)D-Trp | D-Arg | " |
| 11 | " | (5F)D-Trp | (4gua)D-Phe | " |
| 12 | " | (5Cl)D-Trp | D-His | " |
| 13 | dehydro Pro | (6NO$_2$)D-Trp | D-Leu | NHCH$_2$CH$_3$ |
| 14 | D-Trp | (5F)D-Trp | D-Phe | " |
| 15 | D-pGlu | (5F)D-Trp | D-Ile | D-Ala-NH$_2$ |
| 16 | D-Phe | (6NO$_2$)D-Trp | D-Val | NHNHCONH$_2$ |

For purposes of an example, a representative solid phase synthesis of Peptide No. 1 above, which is referred to as [Ac-β-D-2NAL$^1$, (4F)D-Phe$^2$, (6NO$_2$)D-Trp$^3$, D-Arg$^6$]-GnRH is set forth hereinafter. This peptide has the following formula: Ac-β-D-2NAL-(4F)D-Phe-(6NO$_2$)D-Trp-Ser-Tyr-D-Arg-Leu-Arg-Pro-Gly-NH$_2$. The other peptides are similarly synthesized and purified.

A BHA resin is used, and Boc-protected Gly is coupled to the resin over a 2-hour period in CH$_2$Cl$_2$ using a 3-fold excess of Boc derivative and DCC as an activating reagent. The glycine residue attaches to the BHA residue by an amide bond.

Following the coupling of each amino acid residue, washing, deblocking and coupling of the next amino acid residue is carried out in accordance with the following schedule using an automated machine and beginning with about 5 grams of resin:

| STEP | REAGENTS AND OPERATIONS | MIX TIMES MIN. |
|---|---|---|
| 1 | CH$_2$Cl$_2$ wash-80 ml. (2 times) | 3 |
| 2 | Methanol(MeOH) wash-30 ml. (2 times) | 3 |
| 3 | CH$_2$Cl$_2$ wash-80 ml. (3 times) | 3 |
| 4 | 50 percent TFA plus 5 percent 1,2-ethanedithiol in CH$_2$Cl$_2$-70 ml. (2 times) | 10 |
| 5 | Isopropyl alcohol + 1% ethanedithiol wash-80 ml. (2 times) | 3 |
| 6 | TEA 12.5 percent in CH$_2$Cl$_2$-70 ml. (2 times) | 5 |
| 7 | MeOH wash-40 ml. (2 times) | 2 |
| 8 | CH$_2$Cl$_2$ wash-80 ml. (3 times) | 3 |
| 9 | Boc-amino acid (10 mmoles) in 30 ml. of either DMF or CH$_2$Cl$_2$, depending upon the solubility of the particular protected amino acid, (1 time) plus DCC (10 mmoles) in CH$_2$Cl$_2$ | 30–300 |
| 10 | MeOH wash-40 ml. (2 times) | 3 |
| 11 | TEA 12.5 percent in CH$_2$Cl$_2$-70 ml. (1 time) | 3 |
| 12 | MeOH wash-30 ml. (2 times) | 3 |
| 13 | CH$_2$Cl$_2$ wash-80 ml. (2 times) | 3 |

After step 13, an aliquot may be taken for a ninhydrin test: if the test is negative, go back to step 1 for coupling of the next amino acid; if the test is positive or slightly positive, go back and repeat steps 9 through 13.

The above schedule is used for coupling of each of the amino acids of the peptide of the invention after the first amino acid has been attached. N$^\alpha$Boc protection is used for each of the remaining amino acids throughout the synthesis. N$\alpha$Boc-$\beta$-D-2NAL is prepared by a method known in the art, e.g. as described in detail in U.S. Pat. No. 4,234,571, issued Nov. 18, 1980. The side chain of Arg is protected with Tos. OBzl is used as a side chain protecting group for the hydroxyl group of Ser. (6NO$_2$)D-Trp is left unprotected. N$^\alpha$Boc-$\beta$-D-2NAL is introduced as the final amino acid. Boc-Arg(Tos) and Boc-(6NO$_2$)D-Trp, which have low solubility in CH$_2$Cl$_2$, are coupled using DMF:CH$_2$Cl$_2$ mixtures.

After deblocking the $\alpha$-amino group at the N-terminal, acetylation is achieved using a large excess of acetic anhydride in dichloromethane. The cleavage of the peptide from the resin and complete deprotection of the side chains takes place very readily at 0° C. with HF. Anisole is added as a scavenger prior to HF treatment. After the removal of HF under vacuum, the resin is extracted with 50% acetic acid, and the washings are lyophilized to provide a crude peptide powder.

Purification of the peptide is then effected by ion exchange chromatography on CMC (Whatman CM 32, using a gradient of 0.05 to 0.3M NH$_4$OAc in 50/50 methanol/water) followed by partition chromatography in a gel filtration column using the elution system: n-Butanol; 0.1N Acetic acid (1:1-volume ratio).

The peptide is judged to be homogeneous using thin layer chromatography and several different solvent systems, as well as by using reversed-phase high pressure liquid chromatography and an aqueous triethylammonium phosphate solution plus acetonitrile. Amino acid analysis of the resultant, purified peptide is consistent with the formula for the prepared structure, showing substantially integer-values for each amino acid in the chain. The optical rotation is measured on a photoelectric polarimeter as $[\alpha]_D^{22} = -31.8° \pm 1(c=1, 50\%$ acetic acid).

The peptides are assayed in vivo and may also be tested in vitro. If performed, in vitro testing is carried out using dissociated rat pituitary cells maintained in culture for 4 days prior to the assay. The levels of LH mediated in response to the application of peptides is assayed by specific radioimmunoassay for rat LH. Control dishes of cells only receive a measure which is 3 nanomolar in GnRH; experimental dishes receive a measure 3 nanomolar in GnRH plus a measure having either the present standard antagonist for comparison purposes i.e. [Ac-dehydro Pro[1], (4-F)D-Phe[2], D-Trp[3,6]]-GnRH or the test peptide, in concentrations ranging from 0.01 to 10 nanomolar. The amount of LH secreted in the samples treated only with GnRH is compared with that secreted by the samples treated with the peptide plus GnRH.

The ability of the test peptide to reduce the amount of LH released by 3 nanomolar GnRH is compared to that of the present standard peptide. The results are calculated using 3-5 doses of each of the peptides by the statistical program BIOPROG (provided by D. Rodbard NICHD) and are expressed as a potency relative to the present standard. The standard peptide usually blocks 50% of the LH released by GnRH at less than a ratio of $$\frac{0.1 \text{ [antagonist]}}{1 \text{[GnRH]}}.$$

The in vivo testing determines effectiveness to prevent ovulation in female rats. In this test, a specified number of mature female Sprague-Dawley rats, i.e. six, each having a body weight from 225 to 250 grams, is injected with a specified microgram dosage of peptide in corn oil at about noon on the day of proestrous. Proestrus is the afternoon of ovulation. A separate female rat group is used as a control to which the peptide is not administered. Each of the control female rats ovulates on the evening of proestrous; of the rats treated, the number of them which ovulate is recorded. Each of the peptides is considered to be significantly effective to prevent ovulation of female rats at a very low dosage, and each peptide is considered to be totally effective at a dose of about five micrograms. Additional testing is carried out at lower dosages with the results being set forth in TABLE A hereinafter.

TABLE A

| Peptide No. | in vivo Dose (μg) | No. Ovulating |
|---|---|---|
| 1. | 1 | 0/5 |
|  | 0.5 | 4/14 |
| 2. | 1 | 1/10 |
|  | 0.25 | 7/7 |
| 3. | 2.5 | 2/10 |
|  | 2 | 0/6 |
|  | 1 | 5/5 |
| 4. | 1 | 5/14 |
| 5. | 1 | 7/10 |
| 6. | 2 | 0/10 |
|  | 1 | 6/18 |
| 7. | 1 | 3/9 |
| 8. | 1 | 7/14 |
|  | 0.5 | 2/7 |
| 9. | 2.5 | 0/10 |
|  | 1 | 10/16 |
| 10. | 1 | 0/10 |
|  | 0.5 | 9/17 |

All peptides listed in Table I are considered effective to block GnRH-induced LH secretion in vitro at some reasonable concentration. Many of these peptides are much more potent in vivo than the present standard. All of the peptides are considered to be effective to prevent ovulation of female mammals at very low dosages, and some selected ones are considered to be at least twice as potent as any GnRH antagonists previously known and tested.

EXAMPLE II

Peptides as indicated in TABLE II having the formula:

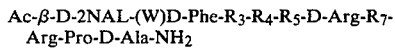

Ac-β-D-2NAL-(W)D-Phe-$R_3$-$R_4$-$R_5$-D-Arg-$R_7$-Arg-Pro-D-Ala-$NH_2$ are prepared by the solid-phase procedure referred to above.

TABLE II

| | W | $R_3$ | $R_4$ | $R_5$ | $R_7$ |
|---|---|---|---|---|---|
| 17 | 4Br | (6$NO_2$)D-Trp | Ser | Tyr | Nle |
| 18 | " | " | " | (2F)Phe | Leu |
| 19 | " | " | AAL | Tyr | Nva |
| 20 | 4Cl | " | aBu | " | Nle |
| 21 | " | (1For)D-Trp | Ser | " | " |
| 22 | " | " | " | (2$CH_3$)Phe | Nva |
| 23 | 4F | " | " | " | NML |
| 24 | " | (5Cl)D-Trp | " | (3$CH_3$)Phe | NML ($Ala^{10}$) |
| 25 | " | (5$CH_3$)D-Trp | " | (2Cl)Phe | NML |
| 26 | 4$NO_2$ | " | " | " | " |
| 27 | " | (5F)D-Trp | Orn | Tyr | Nle |
| 28 | 2,4$Cl_2$ | (5Cl)D-Trp | Ser | (3F)Phe | Nle (acetate salt) |
| 29 | " | (6$NO_2$)D-Trp | AAL | " | Nva |
| 30 | $C^\alpha$Me-4Cl | (5F)D-Trp | Ser | (3I)Tyr | NML |
| 31 | 3,4$Cl_2$ | (5F)D-Trp | Orn | (3Cl)Phe | Leu |

In vitro and/or in vivo testing of the peptides specified in Table II shows that the peptides listed in Table II are considered effective to block GnRH-induced LH secretion in vitro at a reasonable concentration. Many of these peptides are more potent in vivo than the present standard. All of the peptides are considered to be effective to prevent ovulation of female mammals at very low dosages.

EXAMPLE III

Peptides as indicated in TABLE III having the formula:

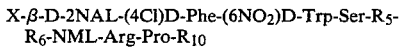

X-β-D-2NAL-(4Cl)D-Phe-(6$NO_2$)D-Trp-Ser-$R_5$-$R_6$-NML-Arg-Pro-$R_{10}$ are prepared by the solid-phase procedure referred to above.

TABLE III

| | X | $R_5$ | $R_6$ | $R_{10}$ |
|---|---|---|---|---|
| 32 | Ac | Tyr | D-Arg | Gly-$NH_2$ |
| 33 | Acr | Arg | D-Tyr | D-Ala-$NH_2$ |
| 34 | For | " | " | $NHCH_2CH_3$ |
| 35 | Bz | (3F)Phe | D-Arg | $NHCH_3$ |
| 36 | Ac | (2F)Phe | D-Lys | $NHCF_3$ |
| 37 | Vac | (2Cl)Phe | D-Har | $NHCH_2CH_2CH_3$ |
| 38 | Acr | (3Cl)Phe | (4gua)D-Phe | $NHCF_2CF_3$ |
| 39 | Ac | (3F)Phe | D-Orn | D-Ala-$NH_2$ |
| 40 | Acr | (3I)Tyr | D-His | " |
| 41 | Ac | Tyr | D-Arg | D-Ala-$NH_2$ ($Pro^8$,$Arg^9$) |
| 42 | " | (3Cl)Phe | " | Gly-$NH_2$ |
| 43 | Vac | " | (4$NH_2$)D-Phe | $NHNHCONH_2$ |

TABLE III-continued

| | X | $R_5$ | $R_6$ | $R_{10}$ |
|---|---|---|---|---|
| 44 | Bz | " | " | $NHNHCONHCH_3$ |

In vitro and/or in vivo testing of the peptides specified in Table III shows that the peptides listed in Table III are considered effective to block GnRH-induced LH secretion in vitro at a reasonable concentration. Many of these peptides are more potent in vivo than the present standard. All of the peptides are considered to be effective to prevent ovulation of female mammals at very low dosages.

The peptides of the invention are often administered in the form of pharmaceutically acceptable, nontoxic salts, such as acid addition salts, or of metal complexes, e.g., with zinc, barium, calcium, magnesium, aluminum or the like (which are considered as addition salts for purposes of this application), or of combinations of the two. Illustrative of such acid addition salts are hydrochloride, hydrobromide, sulphate, phosphate, nitrate, oxalate, fumarate, gluconate, tannate, maleate, acetate, citrate, benzoate, succinate, alginate, malate, ascorbate, tartrate and the like. An aqueous solution of the peptide is repeatedly treated, for example, with 1N acetic acid and then lyophilized to yield the acetic acid salt thereof. If the active ingredient is to be administered in tablet form, the tablet may contain a pharmaceutically-acceptable diluent which includes a binder, such as tragacanth, corn starch or gelatin; a disintegrating agent, such as alginic acid; and a lubricant, such as magnesium stearate. If administration in liquid form is desired, sweetening and/or flavoring may be used as part of the pharmaceutically-acceptable diluent, and intravenous administration is isotonic saline, phosphate buffer solutions or the like may be effected.

The pharmaceutical compositions will usually contain the peptide in conjunction with a conventional, pharmaceutically-acceptable carrier. Usually, the dosage will be from about 1 to about 100 micrograms of the peptide per kilogram of the body weight of the host when given intravenously; oral dosages will be higher. Overall, treatment of subjects with these peptides is generally carried out in the same manner as the clinical treatment using other antagonists of GnRH.

These peptides can be administered to mammals intravenously, subcutaneously, intramuscularly, orally, percutaneously, e.g. intranasally or intravaginally to achieve fertility inhibition and/or control and also in applications calling for reversible suppression of gonadal activity, such as for the management of precocious puberty or during radiation or chemotherapy. Effective dosages will vary with the form of administration and the particular species of mammal being treated. An example of one typical dosage form is a bacteriostatic water solution containing the peptide which solution is administered to provide a dose in the range of about 0.1 to 2.5 mg/kg of body weight. Oral administration of the peptide may be given in either solid form or liquid form.

Although the invention has been described with regard to its preferred embodiments, it should be understood that changes and modifications as would be obvious to one having the ordinary skill in this art may be made without departing from the scope of the invention which is set forth in the claims which are appended hereto. For example, other substitutions known in the art which do not significantly detract from the effectiveness of the peptides may be employed in the peptides of the invention. For instance, instead of the residues specified for $R_{10}$, Gly-OCH$_3$ or Gly-OCH$_2$CH$_3$ or Sar-NH$_2$ (Sar=sarcosine) can be used, or NH-Y can be present, with Y being lower alkyl, cycloalkyl, fluoro lower alkyl or

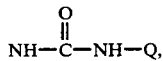

where Q is H or lower alkyl, all of the foregoing being considered to be equivalents.

Particular features of the invention are emphasized in the claims that follow.

What is claimed is:

1. A peptide or a nontoxic salt thereof, said peptide having the formula: X-$R_1$-(W)D-Phe-$R_3$-$R_4$-$R_5$-$R_6$-$R_7$-Arg-Pro-$R_{10}$ wherein X is hydrogen or an acyl group having 7 or less carbon atoms; $R_1$ is dehydro-Pro, D-pGlu, D-Phe, D-Trp or β-D-NAL; W is 4F, 4Cl, 2,4Cl$_2$, 3,4Cl$_2$, 4Br, 4NO$_2$ or C$^\alpha$Me-4Cl; $R_3$ is (N$^{in}$For)D-Trp or D-Trp which is substituted in the 5- or 6-position with NO$_2$, NH$_2$, OCH$_3$, F, Cl, Br or CH$_3$; $R_4$ is Ser, Orn, AAL or aBu; $R_5$ is Tyr, Arg, (3F)Phe, (2F)Phe, (3I)Tyr, (3CH$_3$)Phe, (2CH$_3$)Phe, (3Cl)Phe or (2Cl)Phe; $R_6$ is (4NH$_2$)D-Phe, D-Lys, D-Orn, D-Har, D-His, (4gua)D-Phe, D-Tyr, D-Trp, D-Phe, D-Leu, D-Ile, D-Nle, D-Val, D-Ala, D-Ser(OtBu), β-D-2NAL, (imBzl)D-His, or D-Arg; $R_7$ is Leu, NML, Nle or Nva; and $R_{10}$ is Gly-NH$_2$, D-Ala-NH$_2$ or NH-Y, with Y being lower alkyl, cycloalkyl, fluoro lower alkyl or NHCONHQ, where Q is H or lower alkyl, provided however that when $R_5$ is Arg, $R_6$ is D-Tyr.

2. A peptide in accordance with claim 1 wherein $R_3$ is (6NO$_2$)D-Trp.

3. A peptide in accordance with claim 2 wherein $R_1$ is β-D-2NAL.

4. A peptide in accordance with claim 3 wherein $R_6$ is D-Arg.

5. A peptide in accordance with claim 4 wherein X is acyl.

6. A peptide in accordance with claim 5 wherein $R_{10}$ is D-Ala-NH$_2$.

7. A peptide in accordance with claim 5 wherein $R_{10}$ is Gly-NH$_2$.

8. A peptide in accordance with claim 1 wherein $R_3$ is (N$^{in}$For)D-Trp.

9. A peptide in accordance with claim 2 wherein X is acyl and $R_1$ is dehydro-Pro.

10. A peptide in accordance with claim 9 wherein $R_6$ is β-D-2NAL.

11. A peptide in accordance with claim 1 wherein $R_1$ is β-D-2NAL and X is acyl.

12. A peptide in accordance with claim 11 wherein $R_5$ is (2CH$_3$)Phe.

13. A peptide in accordance with claim 1 wherein $R_3$ is (5OCH$_3$)D-Trp.

14. A peptide in accordance with claim 1 wherein $R_3$ is (N$^{in}$For)D-Trp.

15. A peptide in accordance with claim 1 wherein $R_3$ is (6NH$_2$)D-Trp.

16. A peptide in accordance with claim 1 wherein $R_3$ is (5CH$_3$)D-Trp.

17. A peptide in accordance with claim 1 wherein $R_3$ is (5Cl)D-Trp.

18. A peptide in accordance with claim 1 wherein $R_3$ is (5F)D-Trp.

19. A peptide in accordance with claim 1 wherein $R_3$ is (5Br)D-Trp.

20. A pharmaceutical composition for regulating the secretion of gonadotropins comprising as an active ingredient an effective amount of a peptide having the formula: X-$R_1$-(W)D-Phe-$R_3$-$R_4$-$R_5$-$R_6$-$R_7$-Arg-Pro-$R_{10}$ wherein X is hydrogen or an acyl group having 7 or less carbon atoms; $R_1$ is dehydro-Pro, D-pGlu, D-Phe, D-Trp or β-D-NAL; W is 4F, 4Cl, 2,4Cl$_2$, 3,4Cl$_2$, 4Br, 4NO$_2$ or C$^\alpha$Me-4Cl; $R_3$ is (N$^{in}$For)D-Trp or D-Trp which is substituted in the 5- or 6-position with NO$_2$, NH$_2$, OCH$_3$, F, Cl, Br or CH$_3$; $R_4$ is Ser, Orn, AAL or aBu; $R_5$ is Tyr, Arg, (3F)Phe, (2F)Phe, (3I)Tyr, (3CH$_3$)Phe, (2CH$_3$)Phe, (3Cl)Phe or (2Cl)Phe; $R_6$ is (4NH$_2$)D-Phe, D-Lys, D-Orn, D-Har, D-His, (4gua)D-Phe, D-Tyr, D-Trp, D-Phe, D-Leu, D-Ile, D-Nle, D-Val, D-Ala, D-Ser(OtBu), β-D-2NAL, (imBzl)D-His, or D-Arg; $R_7$ is Leu, NML, Nle or Nva; and $R_{10}$ is Gly-NH$_2$, D-Ala-NH$_2$ or NH-Y, with Y being lower alkyl, cycloalkyl, fluoro lower alkyl or NHCONHQ, where Q is H or lower alkyl, provided however that when $R_5$ is Arg, $R_6$ is D-Tyr; in a pharmaceuticaly-acceptable carrier.

21. A peptide or a nontoxic salt thereof, said peptide having the formula: X-β-D-NAL-(W)D-Phe-$R_3$-$R_4$-$R_5$-$R_6$-$R_7$-Arg-Pro-$R_{10}$ wherein X is hydrogen or an acyl group having 7 or less carbon atoms; W is 4F, 4Cl, 2,4Cl$_2$, 3,4Cl$_2$, 4Br, 4NO$_2$ or C$^\alpha$Me-4Cl; $R_3$ is A(N$^{in}$For)D-Trp, (N$^{in}$AC)D-Trp or D-Trp which is substituted in the 5- or 6-position with NO$_2$, NH$_2$, OCH$_3$, F, Cl, Br or CH$_3$; $R_4$ is Ser, Orn, AAL or aBu; $R_5$ is Tyr, Arg, (3F)Phe, (2F)Phe, (3I)Tyr, (3CH$_3$)Phe, (2CH$_3$)Phe, (3Cl)Phe or (2Cl)Phe; $R_6$ is (4NH$_2$)D-Phe, D-Lys, D-Orn, D-Har, D-His, (4gua)D-Phe, D-Tyr, or D-Arg; $R_7$ is Leu, NML, Nle or Nva; and $R_{10}$ is Gly-NH$_2$, D-Ala-NH$_2$ or NH-Y, with Y being lower alkyl, cycloalkyl, fluoro lower alkyl or NHCONHQ, where Q is H or lower alkyl, provided however that when $R_5$ is Arg, $R_6$ is D-Tyr.

* * * * *

UNITED STATES PATENT AND TRADEMARK OFFICE
CERTIFICATE OF CORRECTION

PATENT NO. : 4,569,927
DATED : February 11, 1986
INVENTOR(S) : Rivier et al.

It is certified that error appears in the above-identified patent and that said Letters Patent is hereby corrected as shown below:

IN THE ABSTRACT

Line 10, "of" should be --or--.

IN THE SPECIFICATION

Column 3, line 15, "D-Try" should be --D-Tyr--.
Column 3, line 42, delete "A".
Column 4, line 6, after "solid" insert --phase--.
Column 4, line 34, correct the spelling of --benzyloxycarbonyl--.
Column 4, line 61, "Try" should be --Tyr--.
Column 10, line 36, "is" should be --in--.
Column 12, line 6, "(5OCH$_3$)Phe" should be --(5OCH$_3$)Phe--.

Signed and Sealed this

Fifth Day of August 1986

[SEAL]

Attest:

DONALD J. QUIGG

Attesting Officer

Commissioner of Patents and Trademarks